US012227585B2

(12) United States Patent
Khandekar et al.

(10) Patent No.: US 12,227,585 B2
(45) Date of Patent: Feb. 18, 2025

(54) ANTI-BCMA ANTIBODY DRUG CONJUGATE COMBINATION TREATMENT FOR CANCER

(71) Applicant: GlaxoSmithKline Intellectual Property Development Limited, Stevenage (GB)

(72) Inventors: Sanjay Khandekar, Collegeville, PA (US); Patrick Mayes, Devon, PA (US); Joanna Opalinska, Collegeville, PA (US)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 0 days.

(21) Appl. No.: 18/453,404

(22) Filed: Aug. 22, 2023

(65) Prior Publication Data
US 2024/0009307 A1 Jan. 11, 2024

Related U.S. Application Data

(63) Continuation of application No. 16/646,875, filed as application No. PCT/IB2018/056968 on Sep. 12, 2018, now abandoned.

(60) Provisional application No. 62/558,593, filed on Sep. 14, 2017.

(51) Int. Cl.
| | |
|---|---|
| C07K 16/28 | (2006.01) |
| A61K 31/454 | (2006.01) |
| A61K 31/573 | (2006.01) |
| A61K 39/395 | (2006.01) |
| A61K 47/68 | (2017.01) |
| A61P 35/00 | (2006.01) |

(52) U.S. Cl.
CPC ........ *C07K 16/2878* (2013.01); *A61K 31/454* (2013.01); *A61K 31/573* (2013.01); *A61K 39/39558* (2013.01); *A61K 47/68031* (2023.08); *A61K 47/6817* (2017.08); *A61K 47/6849* (2017.08); *A61P 35/00* (2018.01)

(58) Field of Classification Search
None
See application file for complete search history.

(56) References Cited

U.S. PATENT DOCUMENTS

| | | | | |
|---|---|---|---|---|
| 9,273,141 | B2 * | 3/2016 | Algate | A61K 47/6803 |
| 9,969,809 | B2 * | 5/2018 | Kuo | A61P 35/04 |
| 2013/0280280 | A1 | 10/2013 | Algate et al. | |
| 2014/0105915 | A1 | 4/2014 | Algate et al. | |
| 2016/0297885 | A1 | 10/2016 | Kuo et al. | |
| 2020/0078404 | A1 | 3/2020 | Ports et al. | |

FOREIGN PATENT DOCUMENTS

| | | |
|---|---|---|
| JP | 2014520088 A | 8/2014 |
| WO | 2012163805 A1 | 12/2012 |
| WO | 2016166629 A1 | 10/2016 |
| WO | 2017093942 A1 | 6/2017 |
| WO | 2018204427 A1 | 11/2018 |

OTHER PUBLICATIONS

Clark et al (2014) (Pomalidomide for the Treatment of Multiple Myeloma, J Adv Pract Oncol, vol. 5 2014), (Year: 2014).*
Tai et al (2014) (Novel anti—B-cell maturation antigen antibody-drug conjugate (GSK2857916) selectively induces killing of multiple myeloma. Blood 2014; vol. 123), (Year: 2014).*
Cohen et al (First in Human Study with GSK2857916, an Antibody Drug Conjugated to Microtubule-Disrupting Agent Directed Against B-Cell Maturation Antigen (BCMA) in Patients with Relapsed/Refractory Multiple Myeloma (MM): Results from Study BMA117159 Part 1 Dose Escalation, Blood, Jan. 2016, vol. 128 (Year: 2016).*
Hechler et al (Abstract 77: Preclinical evaluation of HDP-101, an anti-BCMA antibody-drug conjugate, Cancer Research, Abstracts Jul. 2017). (Year: 2017).*
Clark, et al. "Pomalidomide for the Treatment of Multiple Myeloma", J. Adv. Pract. Oneal., vol. 5, 51-6, 2014.
Cohen, et al., "First in Human Study with GSK2857916, an Antibody Drug Conjugated to Microtubule-Disrupting Agent Directed Against B-Cell Maturation Antigen (BCMA) in Patients with Relapsed/Refractory Multiple Myeloma (MM): Results from Study BMA117159 Part 1 Dose Escalation", Blood, vol. 128, Jan. 2016.
Hechler, et al., "Abstract 77: Preclinical evaluation of HDP-101, an anti-BCMA antibody-drug conjugate", Cancer Research, Abstracts, Jul. 2017.
Kumar, et al., "Lenalidomide, cyclophosphamide, and dexamethasone (CRd) for light-chain amyloidosis: long-term results from a phase 2 trial", Blood, vol. 119, 4860-4867, 2012.
Podar, et al., "Current and developing synthetic pharmacotherapy for treating relapsed/refractory multiple myeloma", Expert Opinion on Pharmacotherapy, vol. 18, No. 11, pp. 1061-1079, Aug. 2017.
Sanchorawala, et al., "Lenalidomide and dexamethasone in the treatment of AL amyloidosis: results of a phase 2 trial", Blood, vol. 109, 492-496, 2007.
Tai, et al., "Novel anti-B-cell maturation antigen antibody-drug conjugate (GSK2857916) selectively induces killing of multiple myeloma", Blood, vol. 123, pp. 3128-3138, 2014.
Tai, et al., "Targeting B-cell maturation antigen in multiple myeloma", Immunotherapy, vol. 7, pp. 1187-1199, 2015.
Trudel, et al., "Targeting B-cell maturation antigen with GSK2857916 antibody drug conjugate in relapsed or refractory multiple myeloma (BMA117159): a dose escalation and expansion phase 1 trial", Lancet Oncology, vol. 19(12), pp. 1641-1653, Dec. 2018.

(Continued)

*Primary Examiner* — Laura B Goddard
*Assistant Examiner* — Sarah A Alsomairy
(74) *Attorney, Agent, or Firm* — Carly Shanahan

(57) ABSTRACT

Disclosed herein is a method of treating cancer, such as multiple myeloma, involving the combination of an anti-BCMA antigen binding protein (e.g., an anti-BCMA antibody) and an immunomodulatory drug (e.g. pomalidomide or lenalidomide). The combinations can also include an anti-inflammatory compound (e.g. dexamethasone).

20 Claims, No Drawings

Specification includes a Sequence Listing.

(56) References Cited

OTHER PUBLICATIONS

Anonymous, "Study NCT03544281 on Date: May 23, 2018 (v1), to Evaluate Safety, Tolerability, and Clinical Activity of the Antibody-drug Conjugate, GSK2857916 Administered in Combination With Lenalidomide Plus Dexamethasone (Arm A), or in Combination With Bortezomib Plus Dexamethasone (Arm B) in Subjects With Rel", ClinicalTrials.gov archive, May 23, 2018: URL:https://clinicaltrials.gov/ct2/history/NCT03544281?V1=View#StudyPageTop [retrieved on Dec. 10, 2018].

Fuchida et al., "Primary Amyloidosis (AL Amyloidosis)," Nippon Rinsho, Multiple Myeloma Science, vol. 74, Extra No. 5, (2016), pp. 540-545.

Rudikoff et al., "Single Amino Acid Substitution Altering Antigen-Binding Specificity," PNAS, vol. 79, (1982), pp. 1979-1983.

Tamura et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology, vol. 164, No. 3, (2000), pp. 1432-1441.

\* cited by examiner

US 12,227,585 B2

ANTI-BCMA ANTIBODY DRUG CONJUGATE COMBINATION TREATMENT FOR CANCER

RELATED APPLICATIONS

This application is a continuation of U.S. application Ser. No. 16/646,875, filed 12 Mar. 2020, which is a national stage application of PCT/IB2018/056968, filed 12 Sep. 2018, which claims the benefit of U.S. Provisional Application No. 62/558,593, filed 14 Sep. 2017, the entireties of each of which are hereby incorporated by reference.

SEQUENCE LISTING

The instant application contains a Sequence Listing which has been submitted electronically in XML file format and is hereby incorporated by reference in its entirety. Said XML copy, created on Aug. 11, 2023, is named PU66429C1-US SL.xml and is 14,504 bytes in size.

FIELD OF THE INVENTION

The present invention relates to methods of treating cancer in a subject. In particular, the present invention relates to a combination of an anti-BCMA antigen binding protein and an immunomodulatory imide drug (IMiD) for treating cancer. Combinations may further include an anti-inflammatory compound, such as dexamethasone.

BACKGROUND TO THE INVENTION

Multiple myeloma (MM) is an incurable malignancy and accounts for 1% of all cancers and for 10% of all hematologic malignancies. A variety of drugs and combination treatments have been evaluated and found effective in treating multiple myeloma (National Comprehensive Cancer Network, 2016; Moreau, San Miguel et al., 2017). However, most, if not all, of these patients inevitably relapse (Richardson, Barlogie et al., 2003; Richardson, Barlogie et al., 2006; Jagannath, Barlogie et al., 2008).

Three and four-drug combinations are emerging for patients with previously treated MM but these regimens may be limited by toxic effects (National Comprehensive Cancer Network, 2016). Agents with new mechanisms of action that can be combined with existing therapies without an increase in serious toxicity are needed. Therefore, there is an urgent need to develop treatment combinations with mechanism of action that do not overlap, and where cross-resistance with prior treatments could be minimized.

SUMMARY OF THE INVENTION

The disclosure relates to methods of treating cancer in a subject, e.g. a human. In particular, the present invention relates to a combination of an anti-BCMA antigen binding protein, such as an antibody, and an immunomodulatory imide drug (IMiD) for treating cancer. Combinations may further include an anti-inflammatory compound such as dexamethasone. In one embodiment, the cancer is selected from multiple myeloma, chronic lymphocytic leukemia, and non-Hodgkin's lymphoma.

Provided herein is a method of treating cancer in a subject in need thereof comprising administering a therapeutically effective dose of a combination comprising an anti-BCMA antigen binding protein and an IMiD. In one embodiment, the combination further comprises an anti-inflammatory compound.

Also provided herein is a method of treating cancer in a subject in need thereof comprising administering a therapeutically effective dose of a combination comprising an anti-BCMA antigen binding protein and an IMiD wherein the antibody comprises a CDRH1 comprising an amino acid sequence with at least 90% sequence identity to the amino acid sequence set forth in SEQ ID NO:1; a CDRH2 comprising an amino acid sequence with at least 90% sequence identity to the amino acid sequence set forth in SEQ ID NO:2; a CDRH3 comprising an amino acid sequence with at least 90% sequence identity to the amino acid sequence set forth in SEQ ID NO:3; a CDRL1 comprising an amino acid sequence with at least 90% sequence identity to the amino acid sequence set forth in SEQ ID NO:4; a CDRL2 comprising an amino acid sequence with at least 90% sequence identity to the amino acid sequence set forth in SEQ ID NO:5; and a CDRL3 comprising an amino acid sequence with at least 90% sequence identity to the amino acid sequence set forth in SEQ ID NO:6.

Further provided herein is a method of treating cancer in a subject in need thereof comprising administering a therapeutically effective dose of a combination comprising an anti-BCMA antigen binding protein and an IMiD, wherein the anti-BCMA antigen binding protein is an antibody comprising a VH comprising an amino acid sequence with at least 90% sequence identity to the amino acid sequence set forth in SEQ ID NO:7; and a VL comprising an amino acid sequence with at least 90% sequence identity to the amino acid sequence set forth in SEQ ID NO:8.

Provided herein is a method of treating cancer in a subject in need thereof comprising administering a therapeutically effective dose of a combination comprising an anti-BCMA antigen binding protein, an IMiD, and an anti-inflammatory compound, wherein the anti-inflammatory compound is dexamethasone.

Also provided herein is a method of treating cancer in a subject in need thereof comprising administering a therapeutically effective dose of a combination comprising an anti-BCMA antigen binding protein and an IMiD, wherein the IMiD is a thalidomide analog. In one embodiment the thalidomide analog is lenalidomide or pomalidomide.

Further provided herein is a method of treating cancer in a subject in need thereof comprising administering a therapeutically effective dose of a combination comprising an anti-BCMA antigen binding protein and an IMiD, wherein the anti-BCMA antigen binding protein is an immunoconjugate comprising an antibody conjugated to a cytotoxin. In one embodiment, the cytotoxin is MMAE or MMAF.

Provided herein is a method of treating cancer, wherein 1.9 mg/kg, 2.5 mg/kg, or 3.4 mg/kg of an anti-BCMA antigen binding protein is administered on day 1 of a 28-day cycle.

Also provided herein is a method of treating cancer, wherein the IMiD is pomalidomide and wherein 4 mg of pomalidomide is administered on days 1-21 of a 28-day cycle.

Further provided herein is a method of treating cancer, wherein the IMiD is lenalidomide and wherein 10 mg or 25 mg of lenalidomide is administered on days 1-21 of a 28-day cycle.

Also provided is a method of treating cancer, wherein the anti-inflammatory compound is dexamethasone and wherein 20 mg or 40 mg of dexamethasone is administered on days 1-4, 9-12, and 17-20 of a 28-day cycle or on days 1, 8, 15, and 22 of a 28-day cycle.

Provided herein is a combination for use in the treatment of cancer, wherein the combination comprises an anti- BCMA antigen binding protein, an IMiD, and, optionally, an anti-inflammatory compound.

Also provided is use of a combination in the manufacture of a medicament for use in the treatment of cancer, wherein the combination comprises an anti-BCMA antigen binding protein, an IMiD, and, optionally, an anti-inflammatory compound.

Provided herein is a kit for use in the treatment of cancer comprising:
(i) an anti-BCMA antigen binding protein;
(ii) instructions for use in the treatment of cancer when combined with an IMiD and an, optionally, anti-inflammatory compound.

Also provided is a method of treating cancer in a human in need thereof comprising administering an anti-BCMA antibody drug conjugate, a thalidomide analog, and optionally, an anti-inflammatory compound.

DETAILED DESCRIPTION OF THE INVENTION

The disclosure relates to methods of treating cancer in a subject. In particular, the present invention relates to a combination of an anti-BCMA antigen binding protein and an IMiD for treating cancer. Combinations may further include an anti-inflammatory compound such as dexamethasone. Without being bound by theory, it is believed that the novel combination(s) described herein result in reduced toxicities due to non-overlapping mechanisms of action.

Combinations and Pharmaceutical Compositions

The term "combination" described herein refers to at least two therapeutic agents. As used herein the term "therapeutic agent" is understood to mean a substance that produces a desired effect in a tissue, system, animal, mammal, human, or other subject. In one embodiment the combination is an anti-BCMA antigen binding protein, suitably an anti-BCMA antibody, and at least one additional therapeutic agent. In one embodiment, the combination is an anti-BCMA antigen binding protein and an IMiD. In another embodiment, the combination is an anti-BCMA antigen binding protein, an IMiD, and an anti-inflammatory compound. The combinations described herein can be effective in treating cancer.

In one embodiment, the combination can contain an additional therapeutic agent, such as, for example, an additional cancer therapeutic agent. In embodiment the additional cancer therapeutic is a proteasome inhibitor such as bortezomib, carfilzomib, ixazomib, or oprozomib.

The administration of the combinations of the invention may be advantageous over the individual therapeutic agents in that the combinations may provide one or more of the following improved properties when compared to the individual administration of a single therapeutic agent alone: i) a greater anticancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, or vi) an increase in the bioavailability of one or both of the therapeutic agents.

The combinations described herein can be in the form of a pharmaceutical composition. A "pharmaceutical composition" contains a combination described herein, and one or more pharmaceutically acceptable carriers, diluents, or excipients. The carrier(s), diluent(s) or excipient(s) must be acceptable in the sense of being compatible with the other ingredients of the formulation, capable of pharmaceutical formulation, and not deleterious to the recipient thereof.

In one embodiment, each therapeutic agent in a combination is individually formulated into its own pharmaceutical composition and each of the pharmaceutical compositions are administered to treat cancer. In this embodiment, each of the pharmaceutical compositions may have the same or different carriers, diluents or excipients. For example, in one embodiment, a first pharmaceutical composition contains an anti-BCMA antigen binding protein, a second pharmaceutical composition contains an IMiD, and the first and second pharmaceutical compositions are both administered to treat cancer. In another embodiment, a first pharmaceutical composition contains an anti-BCMA antigen binding protein, a second pharmaceutical composition contains an IMiD, a third pharmaceutical composition contains an anti-inflammatory compound, and the first, second, and third pharmaceutical compositions are each administered to treat cancer.

In one embodiment, each therapeutic agent in a combination is formulated together into a single pharmaceutical composition and administered to treat cancer. For example, in one embodiment, a single pharmaceutical composition contains both an anti-BCMA antigen binding protein and an IMiD and is administered as a single pharmaceutical composition to treat cancer. In another embodiment, a single pharmaceutical composition contains an anti-BCMA antigen binding protein, an IMiD, and an anti-inflammatory compound and is administered as a single pharmaceutical composition to treat cancer.

It is to be understood that references herein to the IMiDs and anti-inflammatory compounds mean the IMiD and anti-inflammatory compound as the free base, or as a salt, for example a pharmaceutically acceptable salt. Pharmaceutically acceptable salts include acid addition salts. For a review on suitable salts see Berge et al., J. Pharm. Sci., 66:1-19 (1977).

The invention includes within its scope all possible stoichiometric and non-stoichiometric forms of the salts of the IMiD and anti-inflammatory compound.

It will be appreciated that many organic compounds can form complexes with solvents in which they are reacted or from which they are precipitated or crystallized. These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvated include, but are not limited to, NMR and microanalysis. Solvates of the IMiD and anti-inflammatory compounds are within the scope of the invention. As used herein, the term solvate encompasses solvates of both a free base IMiD and anti-inflammatory compound as well as any salt thereof.

Certain IMiDs and anti-inflammatory compounds of the invention may contain chiral atoms and hence may exist in one or more stereoisomeric forms. The present invention encompasses all of the stereoisomers of the IMiDs and anti-inflammatory compounds of the invention, including optical isomers, whether as individual stereoisomers or as mixtures thereof including racemic modifications and mixtures. Any stereoisomer may contain less than 10% by weight, for example less than 5% by weight, or less than 0.5% by weight, of any other stereoisomer. For example, any optical isomer may contain less than 10% by weight, for example less than 5% by weight, or less than 0.5% by weight, of its antipode.

Certain IMiDs and anti-inflammatory compounds of the invention may exist in tautomeric forms. It will be understood that the present invention encompasses all of the tautomers of the IMiDs and anti-inflammatory compounds of the invention whether as individual tautomers or as mixtures thereof.

The IMiD and anti-inflammatory compound of the invention may be in crystalline or amorphous form. Furthermore, some of the crystalline forms of the IMiD and anti-inflammatory compound of the invention may exist as polymorphs, all of which are included within the scope of the present invention. The most thermodynamically stable polymorphic form or forms of the IMiD and anti-inflammatory compound of the invention are of particular interest.

Polymorphic forms of the IMiD and anti-inflammatory compound of the invention may be characterized and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

The present invention also includes all suitable isotopic variations of the IMiD and anti-inflammatory compound or a pharmaceutically acceptable salt thereof. An isotopic variation of the IMiDs and anti-inflammatory compounds, or a pharmaceutically acceptable salt thereof, is defined as one in which at least one atom is replaced by an atom having the same atomic number but an atomic mass different from the atomic mass usually found in nature. Examples of isotopes that can be incorporated into IMiDs and anti-inflammatory compounds of the invention include isotopes of hydrogen, carbon, nitrogen, oxygen, fluorine and chlorine such as $^{2}H$, $^{3}H$, $^{13}C$, $^{14}C$, $^{15}N$, $^{17}O$, $^{18}O$, $^{18}F$ and $^{36}Cl$, respectively. Certain isotopic variations of the IMiD and anti-inflammatory compound or a salt or solvate thereof, for example, those in which a radioactive isotope such as 3H or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the IMiDs, or a pharmaceutically salt thereof, can generally be prepared by conventional procedures.

It will be appreciated from the foregoing that included within the scope of the invention are solvates, hydrates, isomers and polymorphic forms of the IMiD and anti-inflammatory compound and salts and solvates thereof.

It will be appreciated by those skilled in the art that certain derivatives of the IMiD and anti-inflammatory compound, whilst not necessarily possessing pharmacological activity as such, may be administered and thereafter metabolised in the body to form IMiDs and anti-inflammatory compounds that are pharmacologically active. Such derivatives are herein referred to as "prodrugs". Accordingly, the IMiD and anti-inflammatory compound described herein may exist in the form of a prodrug. Examples of suitable derivatives are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1.

Anti-BCMA Antigen Binding Proteins

The anti-BCMA antigen binding proteins in the combinations described herein are useful in the treatment or prevention of cancers. Any of the anti-BCMA antigen binding proteins disclosed herein may be used in combination with an IMiD or in combination with an IMiD and an anti-inflammatory compound for treating cancer. The anti-BCMA antigen binding proteins described herein may bind to human BCMA having, including, for example, human BCMA containing the amino acid sequence of GenBank Accession Number Q02223.2, or genes encoding human BCMA having at least 90 percent homology or at least 90 percent identity thereto.

The term "antigen binding protein" as used herein refers to antibodies, antibody fragments and other protein constructs which are capable of binding to human BCMA. The antigen binding proteins of the present invention may comprise heavy chain variable regions and light chain variable regions of the invention which may be formatted into the structure of a natural antibody or functional fragment or equivalent thereof. An antigen binding protein of the invention may therefore comprise the VH regions of the invention formatted into a full length antibody, a (Fab')2 fragment, a Fab fragment, or equivalent thereof (such as scFV, bi- tri- or tetra-bodies, Tandabs etc.), when paired with an appropriate light chain. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. Furthermore, the antigen binding protein may comprise modifications of all classes e.g. IgG dimers, Fc mutants that no longer bind Fc receptors or mediate C1q binding. The antigen binding protein may also be a chimeric antibody of the type described in WO86/01533 which comprises an antigen binding region and a non-immunoglobulin region.

In another aspect the antigen binding protein is selected from the group consisting of a dAb, Fab, Fab', F(ab')2, Fv, diabody, triabody, tetrabody, miniantibody, and a minibody. In one aspect of the present invention the antigen binding protein is a humanised or chimaeric antibody, in a further aspect the antibody is humanised. In one aspect the antibody is a monoclonal antibody.

Chimeric antigen receptors (CARs) have been developed as artificial T cell receptors to generate novel specificities in T cells without the need to bind to MHC-antigenic peptide complexes. These synthetic receptors contain a target binding domain that is associated with one or more signalling domains via a flexible linker in a single fusion molecule. The target binding domain is used to target the T cell to specific targets on the surface of pathologic cells and the signalling domains contain molecular machinery for T cell activation and proliferation. The flexible linker which passes through the T cell membrane (i.e. forming a transmembrane domain) allows for cell membrane display of the target binding domain of the CAR. CARs have successfully allowed T cells to be redirected against antigens expressed at the surface of tumour cells from various malignancies including lymphomas and solid tumours (Jena et al. (2010) Blood, 116(7): 1035-44).

The development of CARs has comprised three generations so far. The first generation CARs comprised target binding domains attached to a signalling domain derived from the cytoplasmic region of the CD3zeta or the Fc receptor gamma chains. First generation CARs were shown to successfully redirect T cells to the selected target, however, they failed to provide prolonged expansion and anti-tumor activity in vivo. The second and third generation CARs have focused on enhancing modified T cell survival and increasing proliferation by including co-stimulatory molecules, such as CD28, OX-40 (CD134) and 4-1BB (CD137).

T cells bearing CARs could be used to eliminate pathologic cells in a disease setting. One clinical aim would be to transform patient cells with recombinant DNA containing an expression construct for the CAR via a vector (e.g. a lentiviral vector) following aphaeresis and T cell isolation. Following expansion of the T cells they are re-introduced into the patient with the aim of targeting and killing the pathologic target cells.

In one aspect of the invention the anti-BCMA antigen binding protein is a chimeric antigen receptor. In a further aspect the CAR comprises a binding domain, a transmembrane domain and an intracellular effector domain.

In one aspect, the transmembrane domain can be derived either from a natural or from a synthetic source. In one aspect, the transmembrane domain can be derived from any membrane-bound or transmembrane protein. Alternatively the transmembrane domain can be synthetic and can comprise predominantly hydrophobic residues such as leucine and valine. For example, the transmembrane domain can be the transmembrane domain of CD proteins, such as CD4, CD8, CD3 or CD28, a subunit of the T cell receptor, such as $\alpha$, $\beta$, $\gamma$ or $\delta$, a subunit of the IL-2 receptor ($\alpha$ chain), a submit of the Low-Affinity Nerve Growth Factor Receptor (LNGFR or p75) ($\beta$ chain or $\gamma$ chain), or a subunit chain of Fc receptors.

In one aspect, the transmembrane domain comprises the transmembrane domain of CD4, CD8 or CD28. In a further aspect, the transmembrane domain comprises the transmembrane domain of CD4 or CD8 (e.g. the CD8 alpha chain, as described in NCBI Reference Sequence: NP_001139345.1, incorporated herein by reference). In a yet further aspect, the transmembrane domain comprises the transmembrane domain of CD4.

The intracellular effector domain or "signalling domain" is responsible for intracellular signalling following the binding of the target binding domain to the target. The intracellular effector domain is responsible for the activation of at least one of the normal effector functions of the immune cell in which the CAR is expressed. For example, the effector function of a T cell can be a cytolytic activity or helper activity including the secretion of cytokines. Preferred examples of the effector domain for use in a CAR scaffold can be the cytoplasmic sequences of the natural T cell receptor and co-receptors that act in concert to initiate signal transduction following antigen binding, as well as any derivate or variant of these sequences and any synthetic sequence that has the same functional capability.

Effector domains can be separated into two classes: those that initiate antigen-dependent primary activation, and those that act in an antigen-independent manner to provide a secondary or costimulatory signal. Primary activation effector domains can comprise signalling motifs which are known as immunoreceptor tyrosine-based activation motifs (ITAMs). ITAMs are well defined signalling motifs, commonly found in the intracytoplasmic tail of a variety of receptors, and serve as binding sites for syk/zap70 class tyrosine kinases. Examples of ITAMs used in the invention can include, as non-limiting examples, those derived from CD3zeta, FcRgamma, FcRbeta, FcRepsilon, CD3gamma, CD3delta, CD3epsilon, CD5, CD22, CD79a, CD79b and CD66d. In one aspect, the intracellular effector domain comprises a CD3zeta signalling domain (also known as CD247). Natural TCRs contain a CD3zeta signalling molecule, therefore the use of this effector domain is closest to the TCR construct which occurs in nature.

In one aspect of the invention the intracellular signalling domain is a CD3 zeta effector domain. Effector domains may also provide a secondary or costimulatory signal. T cells additionally comprise costimulatory molecules which bind to cognate costimulatory ligands on antigen presenting cells in order to enhance the T cell response, for example by increasing proliferation activation, differentiation and the like. Therefore, in one aspect, the intracellular effector domain additionally comprises a costimulatory domain. In a further aspect, the costimulatory domain comprises the intracellular domain of a costimulatory molecule, selected from CD28, CD27, 4-1BB (CD137), OX40 (CD134), ICOS (CD278), CD30, CD40, PD-1 (CD279), CD2, CD7, NKG2C (CD94), B7-H3 (CD276) or any combination thereof. In a yet further aspect, the costimulatory domain comprises the intracellular domain of a costimulatory molecule, selected from CD28, CD27, 4-1BB, OX40, ICOS or any combination thereof.

Exemplary anti-BCMA antigen binding proteins and methods of making the same are disclosed in International Publication No. WO2012/163805 which is incorporated by reference herein in its entirety. Additional exemplary anti-BCMA antigen binding proteins include those described in WO2016/014789, WO2016/090320, WO2016/090327, WO2016/020332, WO2016/079177, WO2014/122143, WO2014/122144, WO2017/021450, WO2016/014565, WO2014/068079, WO2015/166649, WO2015/158671, WO2015/052536, WO2014/140248, WO2013/072415, WO2013/072406, WO2014/089335, US2017/165373, WO2013/154760, and WO2017/051068, each of which is incorporated by reference herein in its entirety.

In one embodiment, the anti-BCMA antigen binding protein has enhanced antibody dependent cell mediated cytotoxic activity (ADCC) effector function. The term "Effector Function" as used herein is meant to refer to one or more of Antibody dependent cell mediated cytotoxic activity (ADCC), Complement-dependent cytotoxic activity (CDC) mediated responses, Fc-mediated phagocytosis and antibody recycling via the FcRn receptor. For IgG antibodies, effector functionalities including ADCC and ADCP are mediated by the interaction of the heavy chain constant region with a family of Fcgamma receptors present on the surface of immune cells. In humans these include FcgammaRI (CD64), FcgammaRII (CD32) and FcgammaRIII (CD16). Interaction between the antigen binding protein bound to antigen and the formation of the Fc/Fcgamma complex induces a range of effects including cytotoxicity, immune cell activation, phagocytosis and release of inflammatory cytokines.

In another embodiment, the anti-BCMA antigen binding proteins described herein inhibit the binding of BAFF and/or APRIL to the BCMA receptor. In another embodiment, the anti-BCMA antigen binding proteins described herein are capable of binding to FcgammaRIIIA or is capable of FcgammaRIIIA mediated effector function.

In one embodiment, the anti-BCMA antigen binding protein is an antibody comprising a heavy chain variable region CDR1 ("CDRH1") comprising an amino acid sequence with at least 90%, 91%, 92%, 93%, 94%, 95%, 96%, 97%, 98%, 99% or 100% sequence identity to the amino acid sequence set forth in SEQ ID NO:1. In one embodiment, the heavy chain variable region CDR1 ("CDRH1") comprises an amino acid sequence with one amino acid variation (variant) to the amino acid sequence set forth in SEQ ID NO:1.

In one embodiment, the anti-BCMA antigen binding protein is an antibody comprising a heavy chain variable region CDR2 ("CDRH2") comprising an amino acid sequence with at least 90%, 91%, 92%, 93%, 94%, 95%, 96%, 97%, 98%, 99% or 100% sequence identity to the amino acid sequence set forth in SEQ ID NO:2. In one embodiment, the heavy chain variable region CDR2 ("CDRH2") comprises an amino acid sequence with one amino acid variation (variant) to the amino acid sequence set forth in SEQ ID NO:2.

In one embodiment, the anti-BCMA antigen binding protein is an antibody comprising a heavy chain variable region CDR3 ("CDRH3") comprising an amino acid sequence with at least 90%, 91%, 92%, 93%, 94%, 95%, 96%, 97%, 98%, 99% or 100% sequence identity to the amino acid sequence set forth in SEQ ID NO:3. In one embodiment, the heavy chain variable region CDR3 ("CDRH3") comprises an amino acid sequence with one amino acid variation (variant) to the amino acid sequence set forth in SEQ ID NO:3.

In one embodiment, the anti-BCMA antigen binding protein is an antibody comprising a light chain variable region CDR1 ("CDRL1") comprising an amino acid sequence with at least 90%, 91%, 92%, 93%, 94%, 95%, 96%, 97%, 98%, 99% or 100% sequence identity to the amino acid sequence set forth in SEQ ID NO:4. In one embodiment, the light chain variable region CDL1 ("CDR1") comprises an amino acid sequence with one amino acid variation (variant) to the amino acid sequence set forth in SEQ ID NO:4.

In one embodiment, the anti-BCMA antigen binding protein is an antibody comprising a light chain variable region CDR2 ("CDRL2") comprising an amino acid sequence with at least 90%, 91%, 92%, 93%, 94%, 95%, 96%, 97%, 98%, 99% or 100% sequence identity to the amino acid sequence set forth in SEQ ID NO:5. In one embodiment, the light chain variable region CDL2 ("CDR2") comprises an amino acid sequence with one amino acid variation (variant) to the amino acid sequence set forth in SEQ ID NO:5.

In one embodiment, the anti-BCMA antigen binding protein is an antibody comprising a light chain variable region CDR3 ("CDRL3") comprising an amino acid sequence with at least 90%, 91%, 92%, 93%, 94%, 95%, 96%, 97%, 98%, 99% or 100% sequence identity to the amino acid sequence set forth in SEQ ID NO:6. In one embodiment, the light chain variable region CDL3 ("CDR3") comprises an amino acid sequence with one amino acid variation (variant) to the amino acid sequence set forth in SEQ ID NO:6.

In one embodiment, the anti-BCMA antigen binding protein is an antibody comprising a CDRH1 comprising an amino acid sequence with at least 90%, 91%, 92%, 93%, 94%, 95%, 96%, 97%, 98%, 99% or 100% sequence identity to the amino acid sequence set forth in SEQ ID NO: 1; CDRH2 comprising an amino acid sequence with at least 90%, 91%, 92%, 93%, 94%, 95%, 96%, 97%, 98%, 99% or 100% sequence identity to the amino acid sequence set forth in SEQ ID NO:2; CDRH3 comprising an amino acid sequence with at least 90%, 91%, 92%, 93%, 94%, 95%, 96%, 97%, 98%, 99% or 100% sequence identity to the amino acid sequence set forth in SEQ ID NO:3; CDRL1 comprising an amino acid sequence with at least 90%, 91%, 92%, 93%, 94%, 95%, 96%, 97%, 98%, 99% or 100% sequence identity to the amino acid sequence set forth in SEQ ID NO:4; CDRL2 comprising an amino acid sequence with at least 90%, 91%, 92%, 93%, 94%, 95%, 96%, 97%, 98%, 99% or 100% sequence identity to the amino acid sequence set forth in SEQ ID NO:5; and/or CDRL3 comprising an amino acid sequence with at least 90%, 910%, 92%, 93%, 94%, 95%, 96%, 97%, 98%, 99% or 100% sequence identity to the amino acid sequence set forth in SEQ ID NO:6.

In one embodiment, the anti-BCMA antigen binding protein is an antibody comprising a heavy chain variable region ("VH") comprising an amino acid sequence with at least 90%, 91%, 92%, 93%, 94%, 95%, 96%, 97%, 98%, 99% or 100% sequence identity to the amino acid sequence set forth in SEQ ID NO:7.

In one embodiment, the anti-BCMA antigen binding protein is an antibody comprising a light chain variable region ("VL") comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the anti-BCMA antigen binding protein is an antibody comprising a VH comprising an amino acid sequence with at least 90%, 91%, 92%, 93%, 94%, 95%, 96%, 97%, 98%, 99% or 100% sequence identity to the amino acid sequence set forth in SEQ ID NO:7; and a VL comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the anti-BCMA antigen binding protein is an antibody comprising a heavy chain region ("HC") comprising an amino acid sequence with at least 90%, 91%, 92%, 93%, 94%, 95%, 96%, 97%, 98%, 99% or 100% sequence identity to the amino acid sequence set forth in SEQ ID NO:9.

In one embodiment, the anti-BCMA antigen binding protein is an antibody comprising a light chain region ("LC") comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the anti-BCMA antigen binding protein is an antibody comprising a HC comprising an amino acid sequence with at least 90%, 91%, 92%, 93%, 94%, 95%, 96%, 97%, 98%, 99% or 100% sequence identity to the amino acid sequence set forth in SEQ ID NO:9; and a LC comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the anti-BCMA antigen binding protein is an immunoconjugate comprising an antigen binding protein according to the invention as herein described including, but not limited to, an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate). In a further embodiment the anti-BCMA antigen binding protein is conjugated to a toxin such as an auristatin, e.g., monomethyl auristatin E (MMAE) or monomethyl auristatin F (MMAF).

In one embodiment, the anti-BCMA antigen binding protein is an immunoconjugate having the following general structure:

$$ABP\text{-}((Linker)_n\text{-}Ctx)_m$$

wherein
    ABP is an antigen binding protein
    Linker is either absent or any a cleavable or non-cleavable linker
    Ctx is any cytotoxic agent described herein
    n is 0, 1, 2, or 3 and
    m is 1, 2, 3, 4, 5, 6, 7, 8, 9 or 10.

Exemplary linkers include 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio)pentanoate (SPP), N-succinimidyl 4-(N-maleimidomethyl)cyclohexane-1 carboxylate (SMCC), and N-Succinimidyl (4-iodo-acetyl) aminobenzoate (SIAB).

In one embodiment, the anti-BCMA antigen binding protein is an immunoconjugate containing a monoclonal antibody linked to MMAE or MMAF. In another embodiment, the anti-BCMA antigen binding protein is an immunoconjugate containing a monoclonal antibody linked to MMAE or MMAF by an MC linker as depicted in the following structures:

pared to a corresponding subject who has not received such dose, results in improved treatment, healing, prevention, or amelioration of a disease, disorder, or side effect, or a decrease in the rate of advancement of a disease or disorder. The term also includes within its scope doses effective to enhance normal physiological function.

Suitable doses of the anti-BCMA antigen binding proteins described herein may be calculated for patients according to their weight, for example suitable doses may be in the range of about 0.1 to about 20 mg/kg, for example about 1 to about 20 mg/kg, for example about 10 to about 20 mg/kg or for example about 1 to about 15 mg/kg, for example about 10 to about 15 mg/kg.

In one embodiment, the therapeutically effective dose of the anti-BCMA antigen binding protein is in the range of about 0.03 mg/kg to about 4.6 mg/kg. In yet another embodiment, the therapeutically effective dose of the anti-BCMA antigen binding protein is 0.03 mg/kg, 0.06 mg/kg, 0.12 mg/kg, 0.24 mg/kg, 0.48 mg/kg, 0.96 mg/kg, 1.92 mg/kg, 3.4 mg/kg, or 4.6 mg/kg. In yet another embodiment, the therapeutically effective dose of the anti-BCMA antigen binding protein is 1.9 mg/kg, 2.5 mg/kg or 3.4 mg/kg.

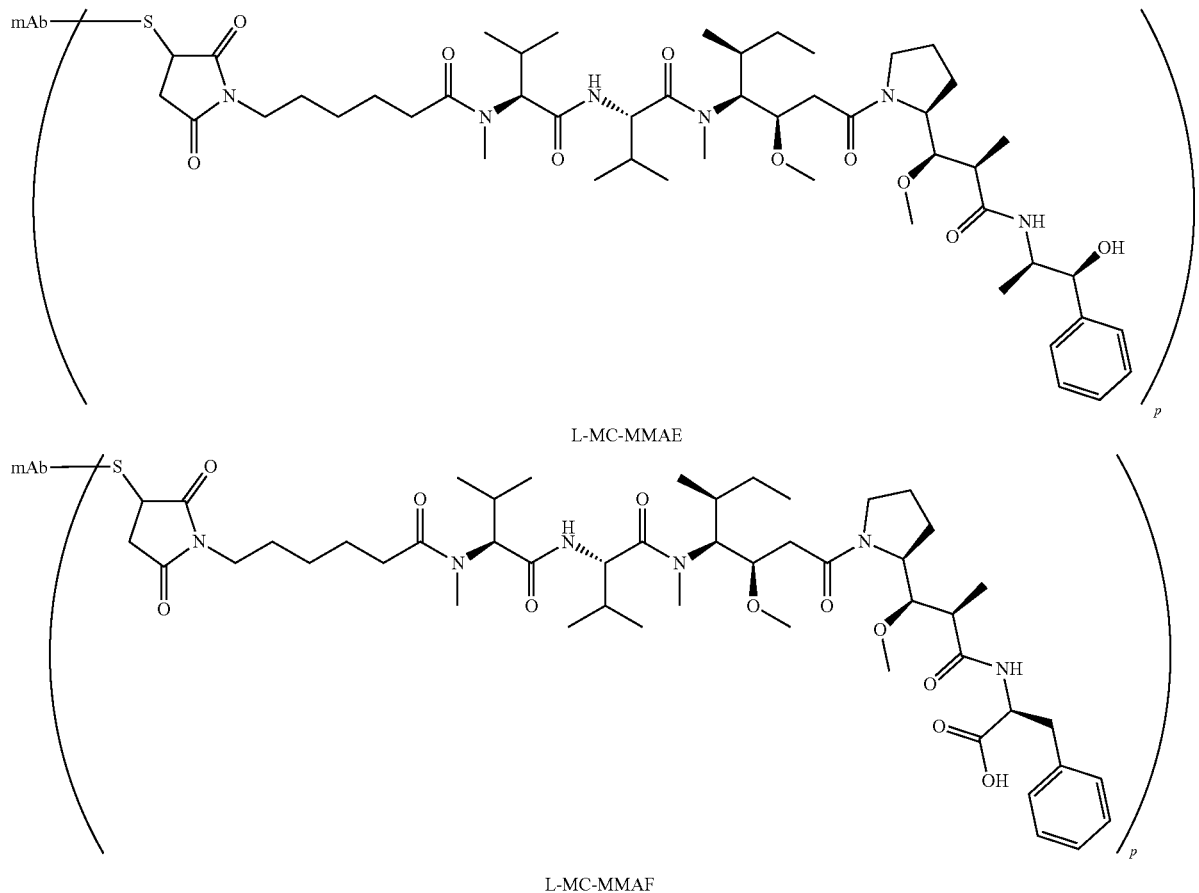

L-MC-MMAE

L-MC-MMAF

The appropriate therapeutically effective dose of the anti-BCMA antigen binding protein will be determined readily by those of skill in the art. As used herein, the term "effective dose" means that dose of a drug or pharmaceutical agent that will elicit the biological or medical response of a tissue, system, animal or human that is being sought, for instance, by a researcher or clinician. Furthermore, the term "therapeutically effective dose" means any dose which, as com- Immunomodulatory Imine Drug (IMiD)

The term "immunomodulatory imine drug (IMiD)" as used herein refers to a class of drugs containing an imide group. Without being bound by theory, it is believed that IMiDs are useful in the treatment of cancers due to immunomodulatory, antiangiogenic, and antineoplastic properties. The IMiD class of drugs includes, but is not limited to, thalidomide and its analogs. The term "analog" as used herein is a compound having a structure similar to that of another one, but differing from it in respect of a certain component, e.g., the analog can differ in one or more atoms, functional groups, or substructures, which are replaced with other atoms, groups, or substructures. Such differences in structure can be imaged, at least theoretically, from the other compound, by one skilled in the art.

Various IMiDs are known to those skilled in the art, including, for example, thalidomide, lenalidomide, pomalidomide, apremilast, and analogs thereof.

In one embodiment, the IMiD includes thalidomide or analogs thereof. Thalidomide is registered under the trade name Thalidomid® (Celgene Corp) and has the following chemical structure:

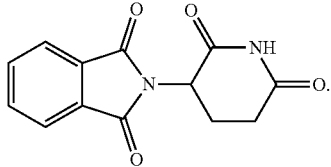 [SMILES: O=C1CCC(N2C(=O)c3ccccc3C2=O)C(=O)N1]

Thalidomide and analogs thereof, and methods of making the same, are known to those skilled in the art, for example, those described in U.S. Pat. Nos. 6,045,501; 7,230,012; 7,435,745, the disclosures of which are incorporated herein in their entireties.

In another embodiment, the IMiD includes pomalidomide or analogs thereof. Pomalidomide is registered under the trade name Pomalyst® (Celgene Corp) and has the following chemical structure:

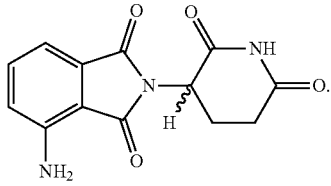 [SMILES: Nc1cccc2c1C(=O)N(C1CCC(=O)NC1=O)C2=O]

Pomalidomide and analogs thereof, and methods of making the same, are known to those skilled in the art, for example, those described in U.S. Pat. Nos. 5,635,517; 6,316,471; 6,476,052; 8,158,653; 8,198,262; 8,673,939; 8,735,428; and 8,828,427 the disclosures of which are incorporated herein in their entireties.

In another embodiment, the IMiD includes lenalidomide or analogs thereof. Lenalidomide is registered under the trade name Revlimid® (Celgene Corp) and has the chemical structure:

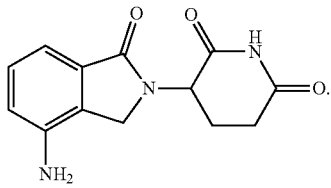 [SMILES: Nc1cccc2c1CN(C1CCC(=O)NC1=O)C2=O]

Lenalidomide and analogs thereof, and methods of making the same, are known to those skilled in the art, for example, those described in U.S. Pat. Nos. 5,635,517; 6,555,554; 7,119,106; 7,465,800; 7,855,217; 8,288,415; and 8,530,498 the disclosures of which are incorporated herein in their entireties.

In another embodiment, the IMiD is apremilast or analogs thereof. Apremilast is registered under the trade name Otezla® (Celgene Corp) and has the following chemical structure:

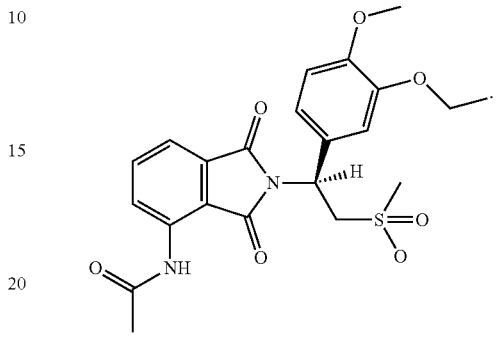

Apremilast and analogs thereof, and methods of making the same, are known to those skilled in the art, for example, those described in U.S. Pat. Nos. 6,020,358; 7,427,638; 7,893,101 the disclosures of which are incorporated herein in their entireties.

The appropriate therapeutically effective dose of the IMiD will be determined readily by those of skill in the art. Suitable doses of the IMiD described herein may be calculated for patients according to their weight. The therapeutically effective dose will generally be between about 1 and 2000 mg, 5 and 2000 mg, 10 and 2000 mg and suitably between about 30 and 1500 mg. Other ranges may be used, including, for example, 50-500 mg, 50-300 mg, 50-100 mg, 100-200 mg, 5-100 mg, 5-50 mg. The therapeutically effective dose as employed for acute or chronic human treatment will range from 0.01 to 250 mg/kg body weight, suitably 0.1-5 mg/kg body weight, suitably 0.1-10 mg/kg body weight, suitably 2-100 mg/kg body weight, or suitably 5-60 mg/kg body weight, which may be administered, for example in one to four daily doses, depending on the route of administration and the condition of the subject.

In one embodiment, the IMiD is thalidomide and the therapeutically effective dose is in the range of about 25 mg to about 300 mg. In another embodiment, the IMiD is thalidomide and the therapeutically effective dose is 50 mg, 100 mg, 150 mg, or 200 mg. In yet another embodiment, the IMiD is thalidomide and the therapeutically effective dose is 200 mg.

In one embodiment, the IMiD is pomalidomide and the therapeutically effective dose is in the range of about 0.5 mg to about 5 mg. In another embodiment, the IMiD is pomalidomide and the therapeutically effective dose is selected from 1 mg, 2 mg, 3 mg, or 4 mg. In yet another embodiment, the IMiD is pomalidomide and the therapeutically effective dose is 4 mg.

In one embodiment, the IMiD is lenalidomide and the therapeutically effective dose is in the range of about 1 mg to about 50 mg. In another embodiment, the IMiD is lenalidomide and the therapeutically effective dose is 2.5 mg, 5 mg, 10 mg, 15 mg, 20 mg, or 25 mg. In yet another embodiment, the IMiD is lenalidomide and the therapeutically effective dose is 10 mg or 25 mg.

In one embodiment, the IMiD is apremilast and the therapeutically effective dose is in the range of about 1 mg to about 100 mg. In another embodiment, the IMiD is apremilast and the therapeutically effective dose is 10 mg, 20 mg, or 30 mg.

Anti-Inflammatory Compound

Anti-inflammatory compounds, such as dexamethasone, are compounds that reduce inflammation or swelling in various parts of the body. Anti-inflammatory compounds have been used to decrease swelling (edema), associated with tumors of the spine and brain, and to treat eye inflammation, as well as treatment for a variety of cancers, such as leukemia, lymphoma, and multiple myeloma. Various anti-inflammatory compounds, and methods of making, are known to those skilled in the art.

Anti-inflammatory compounds can include both steroidal and nonsteroidal compounds (NSAIDs).

In one embodiment, the anti-inflammatory compound is a steroid. Examples of steroids include, but are not limited to, cortisone, cortisol, corticosterone, hydrocortisone, hydrocortisol, prednisone, prednisolone, dexamethasone, beclomethasone, betamethasone, mometasone, mometasone furoate, budesonide, triamcinolone acetonide, and fluticasone. In one embodiment, the anti-inflammatory compound is an adrenal corticosteroid selected from dexamethasone, prednisone, prednisolone, methylprednisone, and methylprednisolone.

In another embodiment, the anti-inflammatory compound is dexamethasone. Dexamethasone has the following chemical structure and is registered under the trade name Decadron® (Merck & Co., Inc.):

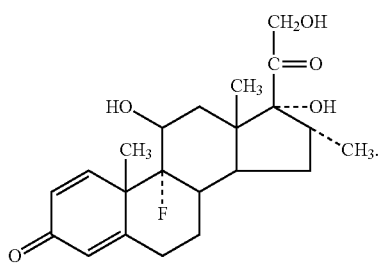

In another embodiment, the anti-inflammatory compound is an NSAID. Examples of NSAIDs which may be used in the invention include, but are not limited to, aspirin, acetominophen, ibuprofen, esculetin, phenidone, quercetin, ketoprofen, nordihydroguiaretic acid. (NDGA), sulindac, sulindac sulfone, sulindac sulfide, indomethacin, NS-398 (a cyclooxygenase-2 inhibitor), cyclooxygenase-1 inhibitors, methylheptyl imidazole, furegrelate sodium, SKF525AHCL, thromboxane inhibitors, toradol, ecasa, salsalate, diflunisal, mefenamic acid, naproxen, naproxen sodium, floctafenine, meclofenamate, phenylbutazone, oxyphenbutazone, diclofenac, etodolac, fenoprofen, flufenamic acid, flurbiprofen, pirprofen, tolmetin, apazone, fenbufen, nabumetone, oxaprozin, piroxicam, salicylate, and tenoxicam. Preferred NSAIDs are sulindac, sulindac sulfone, sulindac sulfide, indomethacin, NS-398, methylheptyl imidazole, furegrelate sodium, and SKF525AHCL. Especially preferred NSAIDs are indomethacin and sulindac.

The appropriate therapeutically effective dose of the anti-inflammatory compound can be determined readily by those of skill in the art. Suitable doses of an anti-inflammatory compound described herein may be calculated for patients according to their weight. The therapeutically effective dose will generally be between about 1 and 2000 mg, 5 and 2000 mg, 10 and 2000 mg and suitably between about 30 and 1500 mg. Other ranges may be used, including, for example, 50-500 mg, 50-300 mg, 50-100 mg, 100-200 mg, 5-100 mg, 5-50 mg. The daily dose as employed for acute or chronic human treatment will range from 0.01 to 250 mg/kg body weight, suitably 0.1-5 mg/kg body weight, suitably 0.1-10 mg/kg body weight, suitably 2-100 mg/kg body weight, or suitably 5-60 mg/kg body weight, which may be administered in one to four daily doses, for example, depending on the route of administration and the condition of the subject.

In one embodiment, anti-inflammatory compound dexamethasone and the therapeutically effective dose is about 5 mg to about 100 mg. In another embodiment, the anti-inflammatory compound is dexamethasone and the therapeutically effective dose is 20 mg or 40 mg.

Methods of Treatment

Described herein are methods for treating cancer in a subject with the combinations described herein. As used herein, the terms "cancer," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent B-cell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenstroem's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

The term "treating" and derivatives thereof as used herein, is meant to include therapeutic therapy. In reference to a particular condition, treating means: (1) to ameliorate the condition or one or more of the biological manifestations of the condition; (2) to interfere with (a) one or more points in the biological cascade that leads to or is responsible for the condition or (b) one or more of the biological manifestations of the condition; (3) to alleviate one or more of the symptoms, effects or side effects associated with the condition or one or more of the symptoms, effects or side effects associated with the condition or treatment thereof; (4) to slow the progression of the condition or one or more of the biological manifestations of the condition and/or (5) to cure said condition or one or more of the biological manifestations of the condition by eliminating or reducing to undetectable levels one or more of the biological manifestations of the condition for a period of time considered to be a state of remission for that manifestation without additional treatment over the period of remission. One skilled in the art will understand the duration of time considered to be remission for a particular disease or condition.

Prophylactic therapy is also contemplated. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

"Subject" is defined broadly to include any patient in need of treatment, for example, a patient in need of cancer treatment. A subject may include a mammal. In one embodiment, the subject is a human patient. The subject in need of cancer treatment may include patients from a variety of stages including newly diagnosed, relapsed, refractory, progressive disease, remission, and others. The subject in need of cancer treatment may also include patients who have undergone stem cell transplant or who are considered transplant ineligible.

Subjects may be pre-screened in order to be selected for treatment with the combinations described herein. In one embodiment, a sample from the subject is tested for expression of BCMA prior to treatment with the combinations described herein.

Subjects may have had at least one prior cancer treatment before being treated with the combinations of the present invention. In one embodiment, the subject has been treated with at least 1, at least 2, at least 3, at least 4, at least 5, at least 6, or at least 7 prior cancer treatments before being treated with the combinations of the present invention.

In another embodiment, the subject has newly diagnosed cancer and has had 0 prior treatments before being treated with the combinations of the present invention.

The individual therapeutic agents of the combination of the invention, and pharmaceutical compositions comprising such therapeutic agents may be administered together or separately. When administered separately, this may occur simultaneously or sequentially in any order (by the same or by different routes of administration). Such sequential administration may be close in time or remote in time. The dose of a therapeutic agents of the invention or pharmaceutically acceptable salt thereof and the further therapeutically active agent(s) and the relative timings of administration will be selected in order to achieve the desired combined therapeutic effect.

The therapeutic agents of the invention may be administered by any appropriate route. For some therapeutic agents, suitable routes include oral, rectal, nasal, topical (including buccal and sublingual), vaginal, and parenteral (including subcutaneous, intramuscular, intraveneous, intradermal, intrathecal, and epidural). It will be appreciated that the preferred route may vary with, for example, the condition of the recipient of the combination and the cancer to be treated. It will also be appreciated that each of the agents administered may be administered by the same or different routes and that the therapeutic agents may be formulated together or in separate pharmaceutical compositions.

In one embodiment, one or more therapeutic agents of a combination of the invention are administered intravenously. In another embodiment, one or more therapeutic agents of a combination of the invention are administered intratumorally. In another embodiment, one or more therapeutic agents of a combination of the invention are administered orally. In another embodiment, one or more therapeutic agents of a combination of the invention are administered systemically, e.g., intravenously, and one or more other therapeutic agents of a combination of the invention are administered intratumorally. In another embodiment, all of the therapeutic agents of a combination of the invention are administered systemically, e.g., intravenously. In an alternative embodiment, all of the therapeutic agents of the combination of the invention are administered intratumorally. In any of the embodiments, e.g., in this paragraph, the therapeutic agents of the invention are administered as one or more pharmaceutical compositions.

In one embodiment, the invention provides a method of treating cancer in a subject in need thereof by administering a therapeutically effective dose of a combination described herein.

In one embodiment, the invention provides a method of treating cancer in a subject in need thereof by administering a therapeutically effective dose of a combination comprising an anti-BCMA antigen binding protein and an IMiD.

In one embodiment, the invention provides a method of treating cancer in a subject in need thereof by administering a therapeutically effective dose of a combination comprising an anti-BCMA antigen binding protein, an IMiD, and an anti-inflammatory compound.

In one embodiment, the invention provides a method of treating cancer in a subject in need thereof by administering a therapeutically effective dose of a combination comprising an anti-BCMA antibody and an IMiD, wherein the anti-BCMA antibody comprises a CDRH1 comprising an amino acid sequence with at least 90%, 91%, 92%, 93%, 94%, 95%, 96%, 97%, 98%, 99% or 100% sequence identity to the amino acid sequence set forth in SEQ ID NO:1; a CDRH2 comprising an amino acid sequence with at least 90%, 91%, 92%, 93%, 94%, 95%, 96%, 97%, 98%, 99% or 100% sequence identity to the amino acid sequence set forth in SEQ ID NO:2; a CDRH3 comprising an amino acid sequence with at least 90%, 91%, 92%, 93%, 94%, 95%, 96%, 97%, 98%, 99% or 100% sequence identity to the amino acid sequence set forth in SEQ ID NO:3; a CDRL1 comprising an amino acid sequence with at least 90%, 91%, 92%, 93%, 94%, 95%, 96%, 97%, 98%, 99% or 100% sequence identity to the amino acid sequence set forth in SEQ ID NO:4; a CDRL2 comprising an amino acid sequence with at least 90%, 91%, 92%, 93%, 94%, 95%, 96%, 97%, 98%, 99% or 100% sequence identity to the amino acid sequence set forth in SEQ ID NO:5; and/or a CDRL3 comprising an amino acid sequence with at least 90%, 91%, 92%, 93%, 94%, 95%, 96%, 97%, 98%, 99% or 100% sequence identity to the amino acid sequence set forth in SEQ ID NO:6.

In one embodiment, the invention provides a method of treating cancer in a subject in need thereof by administering a therapeutically effective dose of a combination comprising an anti-BCMA antibody and an IMiD, wherein the anti-BCMA antibody comprises a VH comprising an amino acid sequence with at least 90%, 91%, 92%, 93%, 94%, 95%, 96%, 97%, 98%, 99% or 100% sequence identity to the amino acid sequence set forth in SEQ ID NO:7; and/or a VL comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the invention provides a method of treating cancer in a subject in need thereof by administering a therapeutically effective dose of a combination comprising an anti-BCMA antibody and an IMiD, wherein the anti-BCMA antibody comprises a HC comprising an amino acid sequence with at least 90%, 91%, 92%, 93%, 94%, 95%, 96%, 97%, 98%, 99% or 100% sequence identity to the amino acid sequence set forth in SEQ ID NO:9; and/or a LC comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the invention provides a method of treating cancer in a subject in need thereof by administering a therapeutically effective dose of a combination comprising an anti-BCMA antibody, an IMiD, and an anti-inflammatory compound, wherein the anti-BCMA antibody comprises a CDRH1 comprising an amino acid sequence with at least 90%, 91%, 92%, 93%, 94%, 95%, 96%, 97%, 98%, 99% or 100% sequence identity to the amino acid sequence set forth in SEQ ID NO:1; a CDRH2 comprising an amino acid sequence with at least 90%, 91%, 92%, 93%, 94%, 95%, 96%, 97%, 98%, 99% or 100% sequence identity to the amino acid sequence set forth in SEQ ID NO:2; a CDRH3 comprising an amino acid sequence with at least 90%, 91%, 92%, 93%, 94%, 95%, 96%, 97%, 98%, 99% or 100% sequence identity to the amino acid sequence set forth in SEQ ID NO:3; a CDRL1 comprising an amino acid sequence with at least 90%, 91%, 92%, 93%, 94%, 95%, 96%, 97%, 98%, 99% or 100% sequence identity to the amino acid sequence set forth in SEQ ID NO:4; a CDRL2 comprising an amino acid sequence with at least 90%, 91%, 92%, 93%, 94%, 95%, 96%, 97%, 98%, 99% or 100% sequence identity to the amino acid sequence set forth in SEQ ID NO:5; and/or a CDRL3 comprising an amino acid sequence with at least 90%, 91%, 92%, 93%, 94%, 95%, 96%, 97%, 98%, 99% or 100% sequence identity to the amino acid sequence set forth in SEQ ID NO:6.

In one embodiment, the invention provides a method of treating cancer in a subject in need thereof by administering a therapeutically effective dose of a combination comprising an anti-BCMA antibody, an IMiD, and an anti-inflammatory compound, wherein the anti-BCMA antibody comprising an anti-BCMA antibody and an IMiD, wherein the anti-BCMA antibody comprises a VH comprising an amino acid sequence with at least 90%, 91%, 92%, 93%, 94%, 95%, 96%, 97%, 98%, 99% or 100% sequence identity to the amino acid sequence set forth in SEQ ID NO:7; and/or a VL comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the invention provides a method of treating cancer in a subject in need thereof by administering a therapeutically effective dose of a combination comprising an anti-BCMA antibody, an IMiD, and an anti-inflammatory compound, wherein the anti-BCMA antibody comprises a HC comprising an amino acid sequence with at least 90%, 91%, 92%, 93%, 94%, 95%, 96%, 97%, 98%, 99% or 100% sequence identity to the amino acid sequence set forth in SEQ ID NO:9; and/or a LC comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the invention provides a method of treating cancer in a subject in need thereof by administering a therapeutically effective dose of a combination comprising an anti-BCMA antigen binding protein and thalidomide.

In one embodiment, the invention provides a method of treating cancer in a subject in need thereof by administering a therapeutically effective dose of a combination comprising an anti-BCMA antigen binding protein, thalidomide, and an anti-inflammatory compound.

In one embodiment, the invention provides a method of treating cancer in a subject in need thereof by administering a therapeutically effective dose of a combination comprising an anti-BCMA antigen binding protein and pomalidomide.

In one embodiment, the invention provides a method of treating cancer in a subject in need thereof by administering a therapeutically effective dose of a combination comprising an anti-BCMA antigen binding protein, pomalidomide, and an anti-inflammatory compound.

In one embodiment, the invention provides a method of treating cancer in a subject in need thereof by administering a therapeutically effective dose of a combination comprising an anti-BCMA antigen binding protein and lenalidomide.

In one embodiment, the invention provides a method of treating cancer in a subject in need thereof by administering a therapeutically effective dose of a combination comprising an anti-BCMA antigen binding protein, lenalidomide, and an anti-inflammatory compound.

In one embodiment, the invention provides a method of treating cancer in a subject in need thereof by administering a therapeutically effective dose of a combination comprising an anti-BCMA antigen binding protein and apremilast.

In one embodiment, the invention provides a method of treating cancer in a subject in need thereof by administering a therapeutically effective dose of a combination comprising an anti-BCMA antigen binding protein, apremilast, and an anti-inflammatory compound.

In one embodiment, the invention provides a method of treating multiple myeloma in a subject in need thereof by administering a therapeutically effective dose of a combination comprising an anti-BCMA antibody, thalidomide, and dexamethasone. In another embodiment, the invention provides a method of treating multiple myeloma in a subject in need thereof by administering 1.9 mg/kg, 2.5 mg·kg, or 3.4 mg/kg of an anti-BCMA antibody, 200 mg of thalidomide, and 20 mg or 40 mg of dexamethasone.

In one embodiment, the invention provides a method of treating multiple myeloma in a subject in need thereof by administering a therapeutically effective dose of a combination comprising an anti-BCMA antibody, pomalidomide, and dexamethasone. In another embodiment, the invention provides a method of treating multiple myeloma in a subject in need thereof by administering 1.9 mg/kg, 2.5 mg·kg, or 3.4 mg/kg of an anti-BCMA antibody, 4 mg of pomalidomide, and 20 mg or 40 mg of dexamethasone.

In one embodiment, the invention provides a method of treating multiple myeloma in a subject in need thereof by administering a therapeutically effective dose of a combination comprising an anti-BCMA antibody, lenalidomide, and dexamethasone. In another embodiment, the invention provides a method of treating multiple myeloma in a subject in need thereof by administering 1.9 mg/kg, 2.5 mg·kg, or 3.4 mg/kg of an anti-BCMA antibody, 10 mg or 25 mg of lenalidomide, and 20 mg or 40 mg of dexamethasone.

In one embodiment, the invention provides a method of treating multiple myeloma in a subject in need thereof by administering a therapeutically effective dose of a combination comprising an anti-BCMA antibody, apremilast, and dexamethasone.

In one embodiment, the invention provides a combination, as described herein, for use in therapy.

In one embodiment, the invention provides a combination, as described herein, for use in the treatment of cancer.

In one embodiment, the invention provides a combination, as described herein, for use in the treatment of cancer, wherein the combination comprises an anti-BCMA antigen binding protein and an IMiD.

In one embodiment, the invention provides a combination, as described herein, for use in the treatment of cancer, wherein the combination comprises an anti-BCMA antigen binding protein, an IMiD, and an anti-inflammatory compound.

In one embodiment, the invention provides a combination, as described herein, for use in the treatment of cancer, wherein the combination comprises an anti-BCMA antibody and an IMiD, wherein the anti-BCMA antibody a CDRH1 comprising an amino acid sequence with at least 90%, 91%, 92%, 93%, 94%, 95%, 96%, 97%, 98%, 99% or 100% sequence identity to the amino acid sequence set forth in SEQ ID NO:1; a CDRH2 comprising an amino acid sequence with at least 90%, 91%, 92%, 93%, 94%, 95%, 96%, 97%, 98%, 99% or 100% sequence identity to the amino acid sequence set forth in SEQ ID NO:2; a CDRH3 comprising an amino acid sequence with at least 90%, 91%, 92%, 93%, 94%, 95%, 96%, 97%, 98%, 99% or 100% sequence identity to the amino acid sequence set forth in SEQ ID NO:3; a CDRL1 comprising an amino acid sequence with at least 90%, 91%, 92%, 93%, 94%, 95%, 96%, 97%, 98%, 99% or 100% sequence identity to the amino acid sequence set forth in SEQ ID NO:4; a CDRL2 comprising an amino acid sequence with at least 90%, 91%, 92%, 93%, 94%, 95%, 96%, 97%, 98%, 99% or 100% sequence identity to the amino acid sequence set forth in SEQ ID NO:5; and/or a CDRL3 comprising an amino acid sequence with at least 90%, 91%, 92%, 93%, 94%, 95%, 96%, 97%, 98%, 99% or 100% sequence identity to the amino acid sequence set forth in SEQ ID NO:6.

In one embodiment, the invention provides a combination, as described herein, for use in the treatment of cancer, wherein the combination comprises an anti-BCMA antibody and an IMiD, wherein the anti-BCMA antibody comprises a VH comprising an amino acid sequence with at least 90%, 91%, 92%, 93%, 94%, 95%, 96%, 97%, 98%, 99% or 100% sequence identity to the amino acid sequence set forth in SEQ ID NO:7; and/or a VL comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the invention provides a combination, as described herein, for use in the treatment of cancer, wherein the combination comprises an anti-BCMA antibody and an IMiD, wherein the anti-BCMA antibody has comprises a HC comprising an amino acid sequence with at least 90%, 91%, 92%, 93%, 94%, 95%, 96%, 97%, 98%, 99% or 100% sequence identity to the amino acid sequence set forth in SEQ ID NO:9; and/or a LC comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the invention provides a combination, as described herein, for use in the treatment of cancer, wherein the combination comprises an anti-BCMA antibody, an IMiD, and an anti-inflammatory compound, wherein the anti-BCMA antibody a CDRH1 comprising an amino acid sequence with at least 90%, 91%, 92%, 93%, 94%, 95%, 96%, 97%, 98%, 99% or 100% sequence identity to the amino acid sequence set forth in SEQ ID NO:1; a CDRH2 comprising an amino acid sequence with at least 90%, 91%, 92%, 93%, 94%, 95%, 96%, 97%, 98%, 99% or 100% sequence identity to the amino acid sequence set forth in SEQ ID NO:2; a CDRH3 comprising an amino acid sequence with at least 90%, 91%, 92%, 93%, 94%, 95%, 96%, 97%, 98%, 99% or 100% sequence identity to the amino acid sequence set forth in SEQ ID NO:3; a CDRL1 comprising an amino acid sequence with at least 90%, 91%, 92%, 93%, 94%, 95%, 96%, 97%, 98%, 99% or 100% sequence identity to the amino acid sequence set forth in SEQ ID NO:4; a CDRL2 comprising an amino acid sequence with at least 90%, 91%, 92%, 93%, 94%, 95%, 96%, 97%, 98%, 99% or 100% sequence identity to the amino acid sequence set forth in SEQ ID NO:5; and/or a CDRL3 comprising an amino acid sequence with at least 90%, 91%, 92%, 93%, 94%, 95%, 96%, 97%, 98%, 99% or 100% sequence identity to the amino acid sequence set forth in SEQ ID NO:6.

In one embodiment, the invention provides a combination, as described herein, for use in the treatment of cancer, wherein the combination comprises an anti-BCMA antibody, an IMiD, and an anti-inflammatory compound, wherein the anti-BCMA antibody has comprises a VH comprising an amino acid sequence with at least 90%, 91%, 92%, 93%, 94%, 95%, 96%, 97%, 98%, 99% or 100% sequence identity to the amino acid sequence set forth in SEQ ID NO:7; and/or a VL comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the invention provides a combination, as described herein, for use in the treatment of cancer, wherein the combination comprises an anti-BCMA antibody, an IMiD, and an anti-inflammatory compound, wherein the anti-BCMA antibody comprises a HC comprising an amino acid sequence with at least 90%, 91%, 92%, 93%, 94%, 95%, 96%, 97%, 98%, 99% or 100% sequence identity to the amino acid sequence set forth in SEQ ID NO:9; and/or a LC comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the invention provides a combination, as described herein, for use in the treatment of cancer, wherein the combination comprises an anti-BCMA antigen binding protein and thalidomide.

In one embodiment, the invention provides a combination, as described herein, for use in the treatment of cancer, wherein the combination comprises an anti-BCMA antigen binding protein, thalidomide, and an anti-inflammatory compound.

In one embodiment, the invention provides a combination, as described herein, for use in the treatment of cancer, wherein the combination comprises an anti-BCMA antigen binding protein and pomalidomide.

In one embodiment, the invention provides a combination, as described herein, for use in the treatment of cancer, wherein the combination comprises an anti-BCMA antigen binding protein, pomalidomide, and an anti-inflammatory compound.

In one embodiment, the invention provides a combination, as described herein, for use in the treatment of cancer, wherein the combination comprises an anti-BCMA antigen binding protein and lenalidomide.

In one embodiment, the invention provides a combination, as described herein, for use in the treatment of cancer, wherein the combination comprises an anti-BCMA antigen binding protein, lenalidomide, and an anti-inflammatory compound.

In one embodiment, the invention provides a combination, as described herein, for use in the treatment of cancer, wherein the combination comprises an anti-BCMA antigen binding protein and apremilast.

In one embodiment, the invention provides a combination, as described herein, for use in the treatment of cancer, wherein the combination comprises an anti-BCMA antigen binding protein, apremilast, and an anti-inflammatory compound.

In one embodiment, the invention provides a combination, as described herein, for use in the treatment of multiple myeloma, wherein the combination comprises an anti-BCMA antibody, thalidomide, and dexamethasone. In another embodiment, the invention provides a combination, as described herein, for use in the treatment of multiple myeloma, wherein the combination comprises 1.9 mg/kg, 2.5 mg/kg, or 3.4 mg/kg of anti-BCMA antibody; 200 mg of thalidomide; and 20 mg or 40 mg dexamethasone.

In one embodiment, the invention provides a combination, as described herein, for use in the treatment of multiple myeloma, wherein the combination comprises an anti-BCMA antibody, pomalidomide, and dexamethasone. In another embodiment, the invention provides a combination, as described herein, for use in the treatment of multiple myeloma, wherein the combination comprises 1.9 mg/kg, 2.5 mg/kg, or 3.4 mg·kg of anti-BCMA antibody; 4 mg of pomalidomide; and 20 mg or 40 mg dexamethasone.

In one embodiment, the invention provides a combination, as described herein, for use in the treatment of multiple myeloma, wherein the combination comprises an anti-BCMA antibody, lenalidomide, and dexamethasone. In another embodiment, the invention provides a combination, as described herein, for use in the treatment of multiple myeloma, wherein the combination comprises 1.9 mg/kg, 2.5 mg/kg, or 3.4 mg·kg of anti-BCMA antibody; 10 mg or 25 mg of lenalidomide; and 20 mg or 40 mg dexamethasone.

In one embodiment, the invention provides a combination, as described herein, for use in the treatment of multiple myeloma, wherein the combination comprises an anti-BCMA antibody, apremilast, and dexamethasone.

In one embodiment, provided is the use of a combination in the manufacture of a medicament for use in the treatment of cancer. In another embodiment, provided is the use of a combination in the manufacture of a medicament for use in the treatment of cancer, wherein the combination comprises an anti-BCMA antigen binding protein and an IMiD. In yet another embodiment, provided is the use of a combination in the manufacture of a medicament for use in the treatment of cancer, wherein the combination comprises an anti-BCMA antigen binding protein, an IMiD, and an anti-inflammatory compound.

Treatment Schedules

The appropriate treatment schedule of the anti-BCMA antigen binding protein, the IMiD, and the anti-inflammatory compound will be determined readily by those of skill in the art.

In one exemplary treatment schedule, one dose of the anti-BCMA antigen binding protein is administered every 3 weeks (21 day cycle) for up to 16 cycles. In another exemplary treatment schedule, one dose of the anti-BCMA antigen binding protein is administered once weekly for three consecutive weeks followed by 1 week of rest (28-day cycle) for a maximum of 16 cycles. In yet another exemplary treatment schedule, one dose of anti-BCMA antigen binding protein is administered on day 1 of a 28-day cycle.

In one exemplary embodiment, the IMiD is thalidomide and the treatment schedule includes administration of a single dose daily for 28 days for at least one 28-day cycle. In another embodiment, the IMiD is thalidomide and the treatment schedule includes administration of 200 mg on days 1-28 of a 28-day cycle.

In one exemplary embodiment, the IMiD is lenalidomide and the treatment schedule includes administration of a single dose on each of days 1-21 of a 28-day cycle. In another exemplary embodiment, the IMiD is lenalidomide and the treatment schedule includes administration of 25 mg on each of days 1-21 of a 28-day cycle. In yet another exemplary embodiment, the IMiD is lenalidomide and the treatment schedule includes administration of 10 mg on each of days 1-21 of a 28-day cycle.

In one exemplary embodiment, the IMiD is pomalidomide and the treatment schedule includes administration of a single dose on each of days 1-21 of a 28-day cycle. In another exemplary embodiment, the IMiD is pomalidomide and the treatment schedule includes administration of 4 mg on each of days 1-21 of a 28-day cycle.

In one exemplary embodiment, the anti-inflammatory compound is dexamethasone and the treatment schedule includes administration of one dose of dexamethasone on days 1-4, 9-12, and 17-20 of a 28-day cycle. In another exemplary embodiment, the anti-inflammatory compound is dexamethasone and the treatment schedule includes administration of one dose of dexamethasone on days 1, 8, 15, and 22 of a 28-day cycle. In yet another embodiment, the anti-inflammatory compound is dexamethasone and the treatment schedule includes administration of dexamethasone on days 1, 2, 4, 5, 8, 9, 11, and 12 21-day cycle.

In one exemplary treatment schedule, the treatment schedules includes administration of 1.9 mg/kg, 2.5 mg/kg, or 3.4 mg/kg of an anti-BCMA antigen binding protein on day 1 of a 28-day cycle; administration of 4 mg of pomalidomide on days 1-21 of a 28-day cycle; and, optionally, administration of 20 mg or 40 mg of dexamethasone on days 1-4, 9-12, and 17-20 of a 28-day cycle or on days 1, 8, 15, and 22 of a 28-day cycle.

In another exemplary treatment schedule, the treatment schedules includes administration of 1.9 mg/kg, 2.5 mg/kg, or 3.4 mg/kg of an anti-BCMA antigen binding protein on day 1 of a 28-day cycle; administration 10 mg or 25 mg lenalidomide on days 1-21 of a 28-day cycle; and, optionally, administration of 20 mg or 40 mg of dexamethasone on days 1-4, 9-12, and 17-20 of a 28-day cycle or on days 1, 8, 15, and 22 of a 28-day cycle.

Kits

In some aspects, the disclosure provides a kit for use in the treatment of cancer comprising:
(i) an anti-BCMA antigen binding protein;
(ii) an IMiD; and
(iii) instructions for use in the treatment of cancer.

In some embodiments, the anti-BCMA antigen binding protein and the IMiD are each individually formulated in their own pharmaceutical compositions with one or more pharmaceutically acceptable carriers.

In some aspects, the disclosure provides a kit for use in the treatment of cancer comprising:
(i) an anti-BCMA antigen binding protein;
(ii) an IMiD;
(iii) anti-inflammatory compound; and
(iii) instructions for use in the treatment of cancer.

In some embodiments, the anti-BCMA antigen binding protein, the IMiD, and the anti-inflammatory compound are each individually formulated in their own pharmaceutical compositions with one or more pharmaceutically acceptable carriers.

In some aspects, the disclosure provides a kit for use in the treatment of cancer comprising:
(i) an anti-BCMA antigen binding protein;
(ii) instructions for use in the treatment of cancer when combined with an IMiD.

In some aspects, the disclosure provides a kit for use in the treatment of cancer comprising:
(i) an anti-BCMA antigen binding protein;
(ii) instructions for use in the treatment of cancer when combined with an IMiD and an anti-inflammatory compound.

EXAMPLES

Example 1: Treatment of Multiple Myeloma with an Anti-BCMA Antibody Drug Conjugate, Lenalidomide, and Dexamethasone A Phase I/II study is conducted in human subjects to determine safety, tolerability, and to determine the recommended Phase 2 dose (RP2D) of an anti-BCMA antigen binding protein given in combination with lenalidomide plus dexamethasone in subjects with relapsed/refractory multiple myeloma (RRMM), and to evaluate safety and clinical activity of the RP2D combination treatments in participants with RRMM.

The anti-BCMA antigen binding protein is an anti-BCMA antibody comprising a CDRH1 comprising the amino acid sequence set forth in SEQ ID NO:1; a CDRH2 comprising the amino acid sequence set forth in SEQ ID NO:2; a CDRH3 comprising the amino acid sequence set forth in SEQ ID NO:3; a CDRL1 comprising the amino acid sequence set forth in SEQ ID NO:4; a CDRL2 comprising the amino acid sequence set forth in SEQ ID NO:5; and the CDRL3 comprising an amino acid sequence set forth in SEQ ID NO:6; and is conjugated to monomethyl auristatin F (MMAF) as described in Tai et al Blood. 2014 May 15; 123(20): 3128-3138.

A single treatment cycle consists of 28 days. Subjects not experiencing dose-limiting or intolerable adverse events may continue treatment with the anti-BCMA antigen binging protein for up to 12 cycles and treatment with lenalidomide and dexamethasone for up to 14 cycles The study consists of two parts: Part 1 is a dose escalation study and Part 2 is a dose expansion study.

Study Part 1 is a Dose Escalation phase to evaluate the safety and tolerability of combination dose levels. It is designed to identify the Recommended Phase 2 Dose (RP2D) Dose level of the anti-BCMA antigen binding protein in combination with lenalidomide plus dexamethasone. Subjects are initially tested at 2.5 mg/kg of the anti-BCMA antigen binding protein on Day 1 of the 28-day cycle; 25 mg lenalidomide on Days 1 to 21 of the 28-day cycle; and 40 mg dexamethasone on Days 1, 8, 15, and 22 of the 28-day cycle.

After Cycle 1 is completed the doses of the anti-BCMA antigen binding protein, lenalidomide, and dexamethasone drugs could be adjusted as follows: The anti-BCMA antigen binding protein can be adjusted to 1.9 mg/kg or 3.4 mg/kg; Lenalidomide can be adjusted to 10 mg; and/or Dexamethasone can be adjusted to 20 mg.

A summary of the treatment schedule is provided in Table 1:

TABLE 1

Treatment schedule

| RRMM Patients | Anti-BCMA antigen binding protein | Lenalidomide | Dexamethasone |
| --- | --- | --- | --- |
| Dosage levels: | 1.9 mg/kg, 2.5 mg/kg, or 3.4 mg/kg | 25 mg or 10 mg | 40 mg or 20 mg |
| Dosing Regimen | Day 1 of 28-day Cycle | Days 1 to 21 of 28-day cycle | Days 1, 8, 15, and 22 of 28-day cycle |

In Part 2 (Dose Expansion) additional subjects are enrolled and treated at the RP2D for each of the anti-BCMA antigen binding protein, lenalidomide, and dexamethasone. Safety (AE, ECGs, MM symptoms, and Laboratory assessments), clinical response and changes in symptoms/quality of life are evaluated at the end of Cycle 1 and all subsequent cycles.

SEQUENCE LISTINGS

SEQ. ID. NO. 1-CDRH1
NYWMH

SEQ. ID. NO. 2: CDRH2
ATYRGHSDTYYNQKFKG

SEQ. ID. NO. 3: CDRH3
GAIYDGYDVLDN

SEQ. ID. NO. 4: CDRL1
SASQDISNYLN

SEQ. ID. NO. 5: CDRL2
YTSNLHS

SEQ. ID. NO. 6: CDRL3
QQYRKLPWT

SEQ. ID. NO. 7: heavy chain variable region
QVQLVQSGAEVKKPGSSVKVSCKASGGTFSNYWMHWVRQAPGQGLEWM
GATYRGHSDTYYNQKFKGRVTITADKSTSTAYMELSSLRSEDTAVYYC
ARGAIYDGYDVLDNWGQGTLVTVSS SED. ID. NO. 8: light chain variable region
DIQMTQSPSSLSASVGDRVTITCSASQDISNYLNWYQQKPGKAPKLLI
YYTSNLHSGVPSRFSGSGSGTDFTLTISSLQPEDFATYYCQQYRKLPW
TFGQGTKLEIKR SEQ. ID. NO. 9: heavy chain region
QVQLVQSGAEVKKPGSSVKVSCKASGGTFSNYWMHWVRQAPGQGLEWM
GATYRGHSDTYYNQKFKGRVTITADKSTSTAYMELSSLRSEDTAVYYC
ARGAIYDGYDVLDNWGQGTLVTVSSASTKGPSVFPLAPSSKSTSGGTA
ALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVM
HEALHNHYTQKSLSLSPGK SEQ. ID. NO. 10: light chain region
DIQMTQSPSSLSASVGDRVTITCSASQDISNYLNWYQQKPGKAPKLLI
YYTSNLHSGVPSRFSGSGSGTDFTLTISSLQPEDFATYYCQQYRKLPW
TFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC

The invention claimed is:

1. A method of treating relapsed/refractory multiple myeloma in a human subject that has been treated with at least one prior cancer treatment, the method comprising administering to the human subject:
   1.9 mg/kg, 2.5 mg/kg, or 3.4 mg/kg of an anti-BCMA antibody-drug conjugate on day 1 of a 28-day cycle; wherein the anti-BCMA antibody drug conjugate comprises an antibody comprising the heavy chain amino acid sequence set forth in SEQ ID NO: 9 and the light chain amino acid sequence set forth in SEQ ID NO: 10, and wherein the antibody is conjugated to MMAF;
   4 mg of pomalidomide on days 1-21 of the 28-day cycle; and 20 mg or 40 mg of dexamethasone on days 1, 8, 15, and 22 of the 28-day cycle.

2. The method of claim 1, wherein 1.9 mg/kg of the anti-BCMA antibody-drug conjugate is administered to the human subject on day 1 of the 28-day cycle.

3. The method of claim 1, wherein 2.5 mg/kg of the anti-BCMA antibody-drug conjugate is administered to the human subject on day 1 of the 28-day cycle.

4. The method of claim 1, wherein the human subject has been treated with at least two prior cancer treatments.

5. The method of claim 4, wherein 1.9 mg/kg of the anti-BCMA antibody-drug conjugate is administered to the human subject on day 1 of the 28-day cycle.

6. The method of claim 4, wherein 2.5 mg/kg of the anti-BCMA antibody-drug conjugate is administered to the human subject on day 1 of the 28-day cycle.

7. A method of treating relapsed/refractory multiple myeloma in a human subject, the method comprising administering to the human subject:
   1.9 mg/kg, 2.5 mg/kg, or 3.4 mg/kg of an anti-BCMA antibody-drug conjugate; wherein the anti-BCMA antibody drug conjugate comprises an antibody comprising a heavy chain variable region (VH) sequence as set forth in SEQ ID NO: 7 and a light chain variable region (VL) sequence as set forth in SEQ ID NO: 8, and wherein the antibody is conjugated to MMAF;
   4 mg of pomalidomide; and
   20 mg or 40 mg of dexamethasone.

8. The method of claim 7, wherein the anti-BCMA antibody drug conjugate comprises an antibody comprising the heavy chain amino acid sequence set forth in SEQ ID NO: 9 and the light chain amino acid sequence set forth in SEQ ID NO: 10.

9. The method of claim 7, wherein 1.9 mg/kg of the anti-BCMA antibody-drug conjugate is administered to the human subject.

10. The method of claim 7, wherein 2.5 mg/kg of the anti-BCMA antibody-drug conjugate is administered to the human subject.

11. The method of claim 8, wherein 1.9 mg/kg of the anti-BCMA antibody-drug conjugate is administered to the human subject.

12. The method of claim 8, wherein 2.5 mg/kg of the anti-BCMA antibody-drug conjugate is administered to the human subject.

13. The method of claim 11, wherein 1.9 mg/kg of the anti-BCMA antibody-drug conjugate is administered to the human subject on day 1 of a 28-day cycle.

14. The method of claim 12, wherein 2.5 mg/kg of the anti-BCMA antibody-drug conjugate is administered to the human subject on day 1 of a 28-day cycle.

15. The method of claim 13, wherein 4 mg of pomalidomide is administered to the human subject on days 1-21 of the 28-day cycle.

16. The method of claim 14, wherein 4 mg of pomalidomide is administered to the human subject on days 1-21 of the 28-day cycle.

17. The method of claim 15, wherein 20 mg or 40 mg of dexamethasone is administered to the human subject on days 1, 8, 15, and 22 of the 28-day cycle.

18. The method of claim 16, wherein 20 mg or 40 mg of dexamethasone is administered to the human subject on days 1, 8, 15, and 22 of the 28-day cycle.

19. The method of claim 9, wherein 1.9 mg/kg of the anti-BCMA antibody-drug conjugate is administered to the human subject on day 1 of a 28-day cycle; 4 mg of pomalidomide is administered to the human subject on days 1-21 of the 28-day cycle; and 20 mg or 40 mg of dexamethasone is administered to the human subject on days 1, 8, 15, and 22 of the 28-day cycle.

20. The method of claim 10, wherein 2.5 mg/kg of the anti-BCMA antibody-drug conjugate is administered to the human subject on day 1 a 28-day cycle: 4 mg of pomalidomide is administered to the human subject on days 1-21 of the 28-day cycle; and 20 mg or 40 mg of dexamethasone is administered to the human subject on days 1, 8, 15, and 22 of the 28-day cycle.

* * * * *

UNITED STATES PATENT AND TRADEMARK OFFICE
CERTIFICATE OF CORRECTION

PATENT NO. : 12,227,585 B2
APPLICATION NO. : 18/453404
DATED : February 18, 2025
INVENTOR(S) : Sanjay Khandekar et al.

It is certified that error appears in the above-identified patent and that said Letters Patent is hereby corrected as shown below:

In the Claims

In Claim 20, at Column 32, Line 55, please delete "day 1 a 28-day cycle" and insert in place thereof --day 1 of a 28-day cycle--.

Signed and Sealed this
Eighth Day of April, 2025

Coke Morgan Stewart
*Acting Director of the United States Patent and Trademark Office*

SEQUENCE LISTING

```
Sequence total quantity: 10
SEQ ID NO: 1              moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 1
NYWMH                                                                    5

SEQ ID NO: 2              moltype = AA  length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 2
ATYRGHSDTY YNQKFKG                                                       17

SEQ ID NO: 3              moltype = AA  length = 12
FEATURE                   Location/Qualifiers
REGION                    1..12
                          note = Description of Artificial Sequence: Synthetic peptide
```

```
source                  1..12
                        mol_type = protein
                        organism = synthetic construct
SEQUENCE: 3
GAIYDGYDVL DN                                                                12

SEQ ID NO: 4            moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 4
SASQDISNYL N                                                                 11

SEQ ID NO: 5            moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 5
YTSNLHS                                                                      7

SEQ ID NO: 6            moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 6
QQYRKLPWT                                                                    9

SEQ ID NO: 7            moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 7
QVQLVQSGAE VKKPGSSVKV SCKASGGTFS NYWMHWVRQA PGQGLEWMGA TYRGHSDTYY             60
NQKFKGRVTI TADKSTSTAY MELSSLRSED TAVYYCARGA IYDGYDVLDN WGQGTLVTVS            120
S                                                                          121

SEQ ID NO: 8            moltype = AA   length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 8
DIQMTQSPSS LSASVGDRVT ITCSASQDIS NYLNWYQQKP GKAPKLLIYY TSNLHSGVPS             60
RFSGSGSGTD FTLTISSLQP EDFATYYCQQ YRKLPWTFGQ GTKLEIKR                         108

SEQ ID NO: 9            moltype = AA   length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 9
QVQLVQSGAE VKKPGSSVKV SCKASGGTFS NYWMHWVRQA PGQGLEWMGA TYRGHSDTYY             60
NQKFKGRVTI TADKSTSTAY MELSSLRSED TAVYYCARGA IYDGYDVLDN WGQGTLVTVS            120
SASTKGPSVF PLAPSSKSTS GGTAALGCLV KDYFPEPVTV SWNSGALTSG VHTFPAVLQS            180
SGLYSLSSVV TVPSSSLGTQ TYICNVNHKP SNTKVDKKVE PKSCDKTHTC PPCPAPELLG            240
GPSVFLFPPK PKDTLMISRT PEVTCVVVDV SHEDPEVKFN WYVDGVEVHN AKTKPREEQY            300
NSTYRVVSVL TVLHQDWLNG KEYKCKVSNK ALPAPIEKTI SKAKGQPREP QVYTLPPSRD            360
ELTKNQVSLT CLVKGFYPSD IAVEWESNGQ PENNYKTTPP VLDSDGSFFL YSKLTVDKSR            420
WQQGNVFSCS VMHEALHNHY TQKSLSLSPG K                                          451
```

-continued

```
SEQ ID NO: 10          moltype = AA  length = 214
FEATURE                Location/Qualifiers
REGION                 1..214
                       note = Description of Artificial Sequence: Synthetic
                       polypeptide
source                 1..214
                       mol_type = protein
                       organism = synthetic construct
SEQUENCE: 10
DIQMTQSPSS LSASVGDRVT ITCSASQDIS NYLNWYQQKP GKAPKLLIYY TSNLHSGVPS    60
RFSGSGSGTD FTLTISSLQP EDFATYYCQQ YRKLPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214
```